United States Patent
Haldeman et al.

(10) Patent No.: US 8,000,771 B2
(45) Date of Patent: Aug. 16, 2011

(54) METHOD AND APPARATUS FOR CATHETERIZATION BY DETECTING SIGNALS INDICATING PROXIMITY TO ANATOMICAL FEATURES

(75) Inventors: Paul Craig Haldeman, Murrieta, CA (US); Rodney Salo, Fridley, MN (US); Bruce Tockman, Scandia, MN (US); Gerrard Merrill Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1347 days.

(21) Appl. No.: 10/653,460

(22) Filed: Sep. 2, 2003

(65) Prior Publication Data
US 2005/0049510 A1    Mar. 3, 2005

(51) Int. Cl.
*A61B 5/05* (2006.01)
(52) U.S. Cl. .................................................... 600/424
(58) Field of Classification Search .................. 600/437, 600/424, 459, 463, 474; 73/633
See application file for complete search history.

(56) References Cited

U.S. PATENT DOCUMENTS

| | | | | |
|---|---|---|---|---|
| 2,949,910 A * | 8/1960 | Brown et al. | ................. | 600/528 |
| 4,608,993 A | 9/1986 | Albert | | |
| 5,109,861 A * | 5/1992 | Walinsky et al. | ............. | 600/463 |
| 5,156,157 A | 10/1992 | Valenta, Jr. et al. | | |
| 5,275,166 A | 1/1994 | Vaitekunas et al. | | |
| 5,645,065 A | 7/1997 | Shapiro et al. | | |
| 5,657,760 A * | 8/1997 | Ying et al. | ..................... | 600/439 |
| 5,746,699 A * | 5/1998 | Fredberg et al. | ............... | 600/529 |
| 5,752,518 A * | 5/1998 | McGee et al. | ................ | 600/424 |
| 5,766,151 A * | 6/1998 | Valley et al. | ............. | 604/103.07 |
| 5,830,144 A * | 11/1998 | Vesely | .......................... | 600/459 |
| 5,844,140 A * | 12/1998 | Seale | .............................. | 73/633 |
| 5,908,385 A * | 6/1999 | Chechelski et al. | .......... | 600/374 |
| 6,453,190 B1 * | 9/2002 | Acker et al. | ................... | 600/424 |
| 6,591,130 B2 * | 7/2003 | Shahidi | ........................ | 600/424 |
| 6,705,319 B1 * | 3/2004 | Wodicka et al. | ......... | 128/207.14 |
| 2002/0042632 A1 * | 4/2002 | Iaizzo et al. | .................... | 607/27 |

* cited by examiner

*Primary Examiner* — Long V Le
*Assistant Examiner* — Ellsworth Weatherby
(74) *Attorney, Agent, or Firm* — Hollingsworth & Funk, LLC

(57) ABSTRACT

A guiding catheter for use in medical procedures includes a flexible shaft with one or more audio transducers and a distal tip. An audio signal may be sent to one or more of the transducers and a reflected signal is received at one or more transducers. The reflected signal is used to detect the presence of an anatomical structure to assist in navigating the catheter to its destination. In another arrangement, the transducer can be used passively to detect physical characteristics of the heart such as sound, subsonic energy or temperature, that indicate relative proximity of a destination vessel.

30 Claims, 4 Drawing Sheets

METHOD AND APPARATUS FOR CATHETERIZATION BY DETECTING SIGNALS INDICATING PROXIMITY TO ANATOMICAL FEATURES

FIELD OF THE INVENTION

The invention relates generally to catheter systems, and more particularly to medical guiding catheters.

BACKGROUND

Guiding catheters are instruments that allow a physician to locate and cannulate vessels in a patient's anatomy for performing various medical procedures, including mapping heart vessels (venography) and implanting of cardiac pacing devices. Cannulating heart vessels may require navigating a small diameter, flexible guide through convoluted vasculature into a heart chamber, and then into a destination heart vessel. Once the destination heart vessel is reached, the catheter acts as a conduit for insertion of payloads into the vessel.

Because the guiding catheter must traverse a convoluted path, it can often be difficult to maneuver the catheter to particular vessels. For example, a common target of pacing lead implantation procedures is the coronary sinus accessed from the right atrium of the heart. Maneuvering the guiding catheter into the opening (ostium) of the coronary sinus involves locating a relatively small vessel located at a wall of a larger heart chamber.

Some methods such as fluoroscopy are used to assist in guiding a device into vessels, such as the coronary sinus. Fluoroscopy involves injecting a radiopaque dye into the heart chamber then viewing the heart using radiographic (e.g., X-ray) imaging equipment. However, it is preferable to minimize the patient's exposure to X-rays. Additionally, an imaging technique such as fluoroscopy only provides a two-dimensional view of the target area. The anatomical structures require maneuvering in three dimensional space. This is especially true in relatively large cavities such as heart chambers. Therefore, a system that assists in placing a guiding catheter in a destination vessel with or without the use of fluoroscopy is desirable.

SUMMARY

The present disclosure describes a method and apparatus for catheterization using audio frequency signals, subsonic frequency signals, temperature signals, or other energy parameters indicative of cardiac activity to sense anatomical structures. In one embodiment, guiding catheter includes a flexible shaft having a proximal end and a distal end. A sensor, such as an acoustic sensor, accelerometer or temperature sensor, for example, is provided at the distal end of the guiding catheter to detect an energy parameter associated with cardiac activity. Variations in the detected energy parameter are transduced into a user perceivable representation indicative of a relative proximity between the guiding catheter's distal end and a destination vessel of interest.

In one embodiment, a sound transmitter is configured to transmit an audio frequency signal from the distal end of the flexible shaft. A sound receiver is configured to detect a reflected signal received at the distal end of the flexible shaft. A proximal device is coupled to the sound receiver. The proximal device is arranged to receive the reflected signal and produce a user perceivable representation of a variation in the reflected signal. The variation in the reflected signal indicates a presence of the anatomical features to assist in navigating the distal end of the flexible shaft to the destination vessel.

The guiding catheter may include a steering mechanism. The distal end of the flexible shaft can be deflected by actuation of the steering mechanism at the proximal end of the flexible shaft to steer the catheter in a desired direction. The catheter may include an audio speaker and/or a video display coupled to the catheter and configured to represent the reflected signal. The transmitted audio frequency signal may include a cyclic signal and/or a random signal.

In another embodiment of the present invention, a method of accessing a destination vessel for performing a medical procedure involves introducing a guiding catheter into an access vessel that provides access to the destination vessel. An audio signal is sent from a distal part of the guiding catheter. A reflected signal resulting from the audio signal is detected at a distal part of the guiding catheter. An anatomical structure is detected near the distal tip of the guiding catheter based on a change in the reflected audio signal. The guiding catheter can be navigated to the destination vessel based on a location of the anatomical structure detected by use of the reflected audio signal.

In a further embodiment, an accelerometer or temperature sensor is provided at the distal end of the guiding catheter to detect an energy parameter associated with cardiac activity. Variations in the detected energy parameter are transduced into a user perceivable representation indicative of a relative proximity between the guiding catheter's distal end and a destination vessel of interest.

The above summary is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
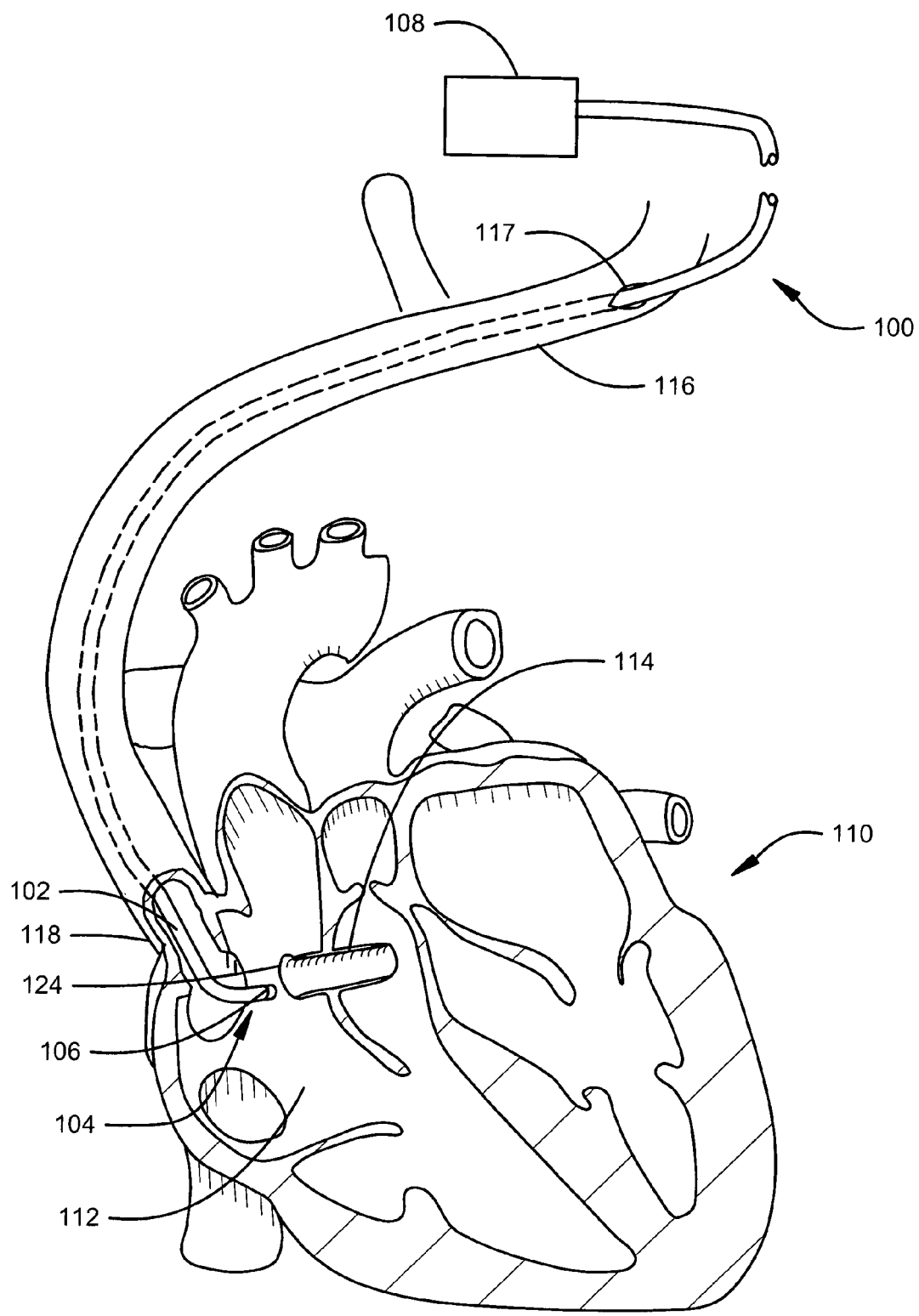
FIG. 1 is a cutaway view of a heart showing a guiding catheter according to various embodiments of the present invention positioned in the right atrium.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In broad and general terms, the present disclosure describes a method and apparatus for guiding catheterization that is suitable for placing devices in anatomical locations such as cardiac vessels. In one embodiment, an apparatus includes a catheter body having one or more audio frequency sound transducers at a distal end. The transducers may be coupled to a proximal device that assists in guiding the catheter by sending signals to the transducers and receiving reflected signals from the transducers. In another embodiment, a transducer may be coupled to a proximal device that assists in guiding the catheter by detecting an energy parameter associated with cardiac activity. The received/detected signals may be interpreted to detect anatomical structures, thereby assisting in placing the catheter in a destination location.

With reference to FIG. 1, a guiding catheter 100 is illustrated according to an embodiment of the present invention. The guiding catheter 100 includes an elongated, flexible body 102 that can be introduced in anatomical passageways to support medical procedures. The medical procedures may include insertion of medical devices into the heart 110, as well as delivery of drugs, sensors, pacing leads, defibrillation leads, or other diagnostic objects into target vessels of the heart 110.

The flexible body 102 includes a distal end 104 that may be introduced into the target vessel. In this example, the distal end 104 is located in the right atrium 112 of the heart 110. The target vessel may include heart vessels such as the coronary sinus 114. The coronary sinus 114 is often accessed through an access vessel 116 of the vasculature such as the cephalic vein. An incision 117 is made in an access vessel 116 and the catheter 100 introduced into the heart 110 from the incision 117. In the illustrated access path, the catheter enters the heart 110 through the superior vena cava 118 and into the right atrium 112.

The guiding catheter 100 includes at least one distally located transducer 106. The transducer 106 may be used for transmission and reception of audio frequency sound into an anatomical region. Although a single transducer 106 may act as both a sound transmitter and sound receiver (i.e., transceiver), typically more than one transducers 106 are employed, each adapted for performing one of the transmitting and receiving functions.

While maneuvering the guiding catheter 100 to its destination, an audio signal is sent to the transducer 106. This signal is reflected from various anatomical features such as tissue. The reflected signal will change in characteristic based on the local presence of anatomical features in a manner well known in the art. These changes can be received by the transducer 106. The received signal is used to assist navigating the catheter shaft 102 to the target location.

The signals sent to the transducers 106 can be generated by a proximal device 108. In other configurations, the signals sent to the transducers 106 may be generated elsewhere, such as from circuitry included on the flexible shaft 102. In such a configuration, the proximal device 108 may be configured to activate the transducer 108, such as by switching the circuit power on and off.

The proximal device 108 may also be configured to receive the reflected signals from the transducers 106. The proximal device 108 may be fully integrated with the catheter 100 or may be provided in full or in part as a separate assembly from the catheter 100. Further, portions of the proximal device 108 such as circuitry may be included at a distal end of the catheter 100.

Figure 2:
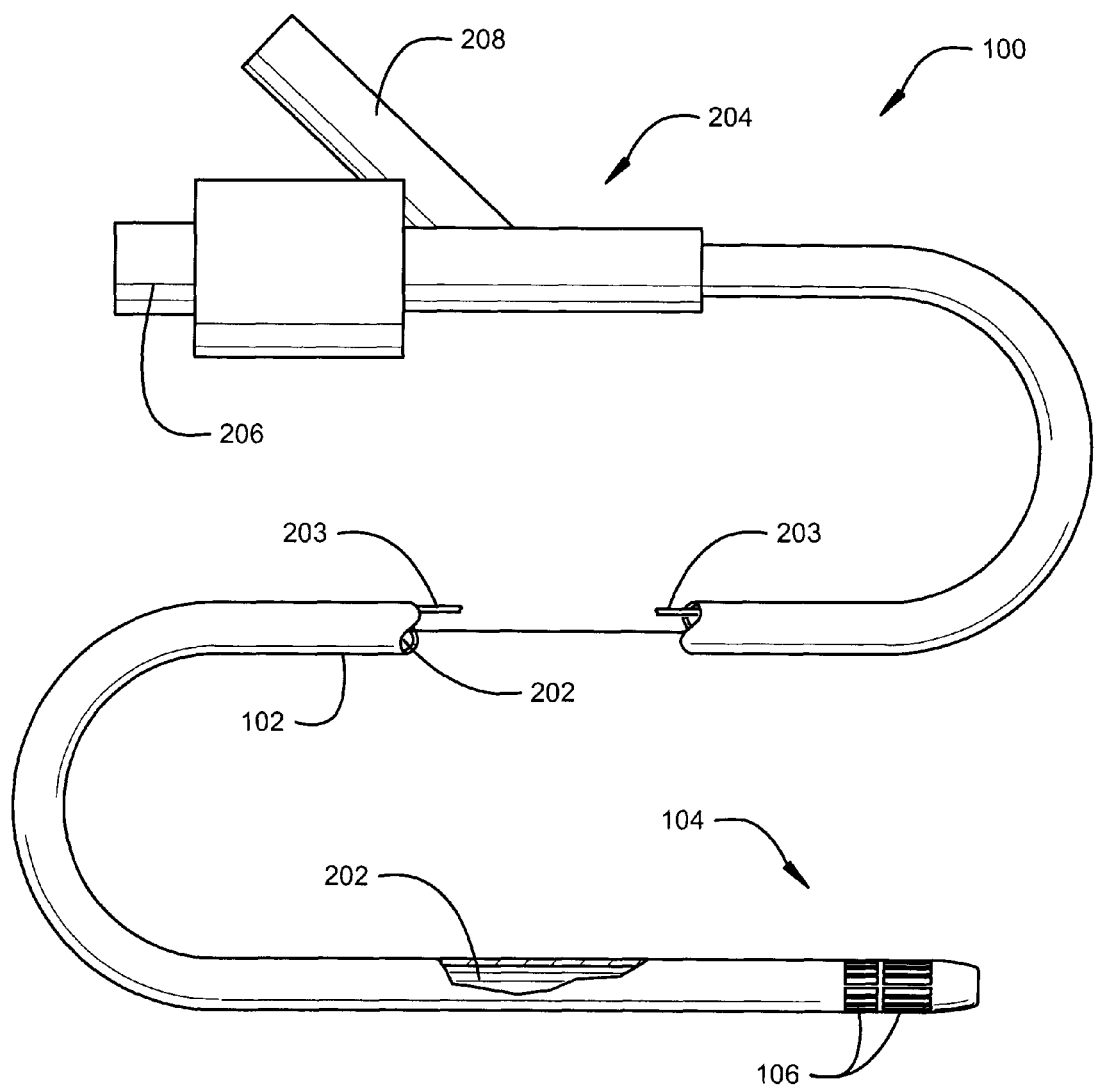
FIG. 2 is a side view of a guiding catheter according to embodiments of the present invention.

FIG. 2 shows a side view of a catheter 100 according to one embodiment of the present invention. The flexible shaft 102 may be formed of any suitable sized flexible tubing, preferably a round polymer tubing with a central, open lumen 202. The lumen 202 may be used to introduce payloads into the target anatomy, such as implantable leads, drugs, sensors, radiopaque fluid, etc. The shaft 102 may include additional lumens (not shown) adapted for containing guide wires, electrical conductors, dye injections, etc.

The flexible shaft 102 may be formed of an extruded tube of a single polymer material. Alternatively, the shaft 102 may be assembled using a multiple-layer construction. Typically, multi-layer shafts will include a core tubing portion with various coatings/layers on inner and outer surfaces to impart desired properties to those surfaces while still keeping the shaft reasonably flexible. Typically, outer surface coatings are chosen to provide an impermeable and smooth outer surface, while inner surfaces may include lubricous coatings which allow easier movement of devices within the lumens. Other features may be included with the shaft 102, such as an embedded stainless steel or fiber braid, which provides longitudinal stiffness.

The flexible shaft 102 is shown supporting an array of transducers 106 at the shaft's distal end 104. The transducers 106 may be any combination of transmitting elements (e.g., speakers) and receiving elements (e.g., microphones). In general, audio frequency transducers 106 are rugged, inexpensive, and based on well-developed technologies. Various useful types of audio transducers 106 are known in the art, including piezoelectric, electrostatic, and electromagnetic transducers. Typically, the choice of transducer 106 will depends on many design factors, including size, material safety, frequency response, bio-compatibility, and sensitivity of the target device.

The transducers 106 in FIG. 2 are shown as small elements arranged in an array around the catheter shaft 102. Other transducers shapes and layouts may be used for receiving and transmitting transducers 106, such as ring shaped or elongated arrangements. The transducers 106 may be electrically operable, and can be coupled to one or more conductors 203. In other arrangements, the transducers 106 may include some form or mechanical, fluid, optical or acoustic coupling along the shaft 102. In other arrangements, one or more transducers 106 may be positioned on any part of the shaft 102 or catheter 100 and be acoustically or mechanically coupled to the distal end 104 of the shaft 102.

The transducers 106 are shown fixably mounted to the flexible shaft 102. In other configurations, the transducers 106 may be included as a separate sleeve or catheter slidable inside or outside the flexible shaft 102. In this arrangement, the transducers 106 may be coupled with the shaft 102 during access procedures, and later slidably removed.

The conductors 203 may be physically and communicatively attached to the transducers 106 at the shaft's distal end 104. The conductors 203 are typically disposed along the catheter shaft 102 through one or more dedicated lumens. The conductors 203 may also be embedded in a wall of the shaft 102 or positioned between layers of a multiple layer shaft 102. The conductors 203 may be formed of any manner of transmitting medium such as wire or fiber optic cable. When the conductors 203 are electrical, electrically shielding may be provided with the conductors. In other arrangements, metallic braids used in the shaft construction may provide shielding.

The conductors 203 may be accessed at a proximal attachment 204. The proximal attachment 204 is coupled to the proximal end of the shaft 102 and provides various interfaces to the shaft. The proximal attachment 204 may include a luer-type fitting 206 that allows introduction of payloads into the shaft lumen 202. A side fitting 208 may also be included and fitted with a luer-type attachment. Either fitting 206, 208 may include coupling points to the conductors 203, or additional signal connectors (not shown) may be included for mating with the conductors 203. The proximal attachment 204 may include electronic circuitry for signal processing. The proximal device 108 (see FIG. 1) may be included entirely within the proximal attachment 204, or may have external components that interface with the attachment 204.

Figure 3:
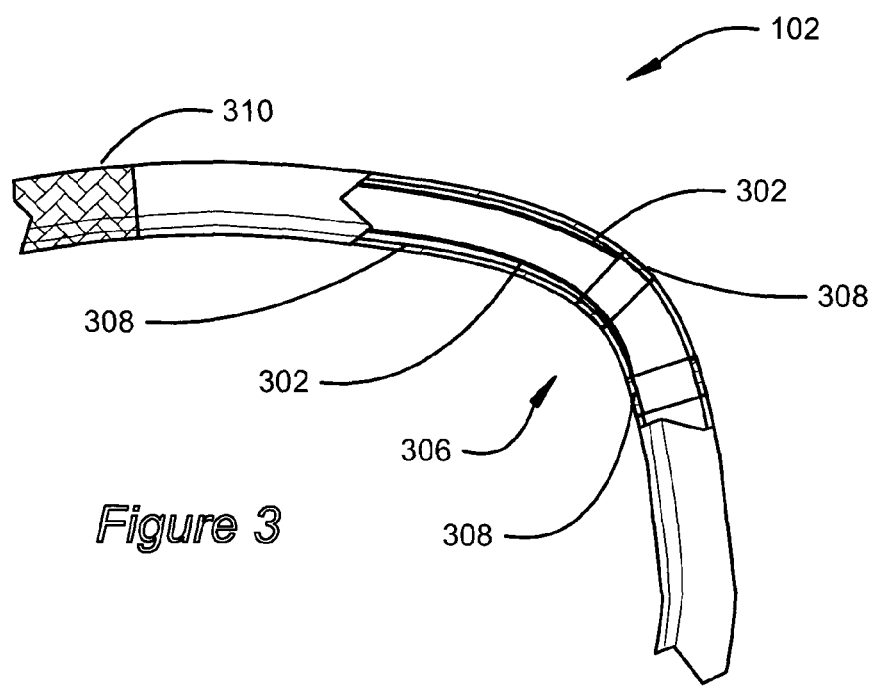
FIG. 3 is a partial cutaway view showing a catheter steering mechanism according to an embodiment of the present invention.

Other features known in the art may be included with the guiding catheter 100. A steering apparatus may be used in the catheter shaft 102 to allow steering of the distal end 102 during access procedures. FIG. 3 illustrates a catheter shaft 102 with an internal steering arrangement. The steering arrangement includes one or more steering tendons 302. The steering tendons 302 may be formed from a metallic or fibrous member. The steering tendons 302 are deployed within the catheter shaft 102, typically in a dedicated lumen (not shown).

In the illustrated arrangement of FIG. 3, two steering tendons 302 are each fixed to an anchor member 308. In other arrangements, each tendon 302 may be affixed to the same anchor member 308. The anchor members 308 may be bands or plugs, and typically serve as a distal attachment points for the steering tendons 302. The anchor members 308 are located distal to a deflection area 306 of the catheter shaft 102. The deflection area 306 may be straight or curved when in a neutral orientation. When a bidirectional steering arrangement is used, the deflection area 306 is preferably straight when in a neutral orientation.

The catheter shaft 102 is typically formed so that it is relatively flexible in an area encompassing at least part of the deflection area 306. A stiffness transition 310 may be included proximal to the deflection area 306. Thus, when a force is applied to one or more of the steering tendons 302, the catheter shaft 102 will deflect in a predictable manner, generally deflecting around the deflection area 306.

Figure 4:
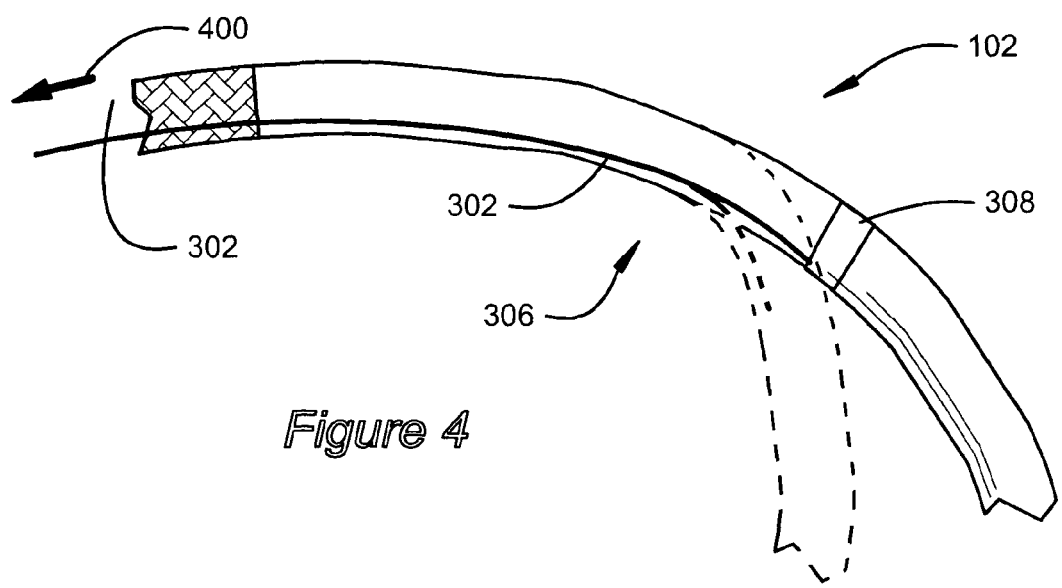
FIG. 4 is a side view of the catheter shaft illustrating steering deflection according to an embodiment of the present invention.

The operation of a steering tendon 302 is illustrated in FIG. 4. The initial shape of the catheter shaft 102 is shown in dashed lines. The single tendon 302 can be pulled in the direction of the arrow 400, causing the shaft 102 to deflect to the indicated shape. Steering with a single tendon 302 as shown in FIG. 2 provides unidirectional steering control. When additional tendons 302 are included as shown in FIG. 3, multidirectional steering modes may be provided.

Referring again to FIG. 1, guiding the catheter 100 generally involves activating a transducer 106 to send a signal from the shaft's distal end 104, analyzing reflected signals detected by a transducer 106 and sent to the proximal device 108, and maneuvering the flexible shaft 102 into position based on the changes detected in the reflected signals. The shaft 102 may be maneuvered by manipulation (e.g. pushing, twisting) at a proximal end of the catheter 100, as well as using a steering apparatus as described in relation to FIGS. 3 and 4.

The reflected signals are typically communicated to the user at the proximal device 108. This communication may be made by any combination of audible, visual, or tactile feedback provided to the user. The proximal device may include or be coupled to any combination of speaker, headphone, display, vibrating element, or other sensory transducer that can be configured to communicate various aspects of the reflected signal in a manner perceivable by the user.

Often, a trained ear can discern properties of a reflected audio frequency signal by listening to the reflected signal. Therefore, the following description uses examples of audio circuits for purposes of illustrating detection methods according to embodiments of the present invention. It will be appreciated by those skilled in the art that the concepts described may be applied to other methods of signal analysis and interpretation, including digital signal processing, and translation to visual and tactile representations.

Figure 5:
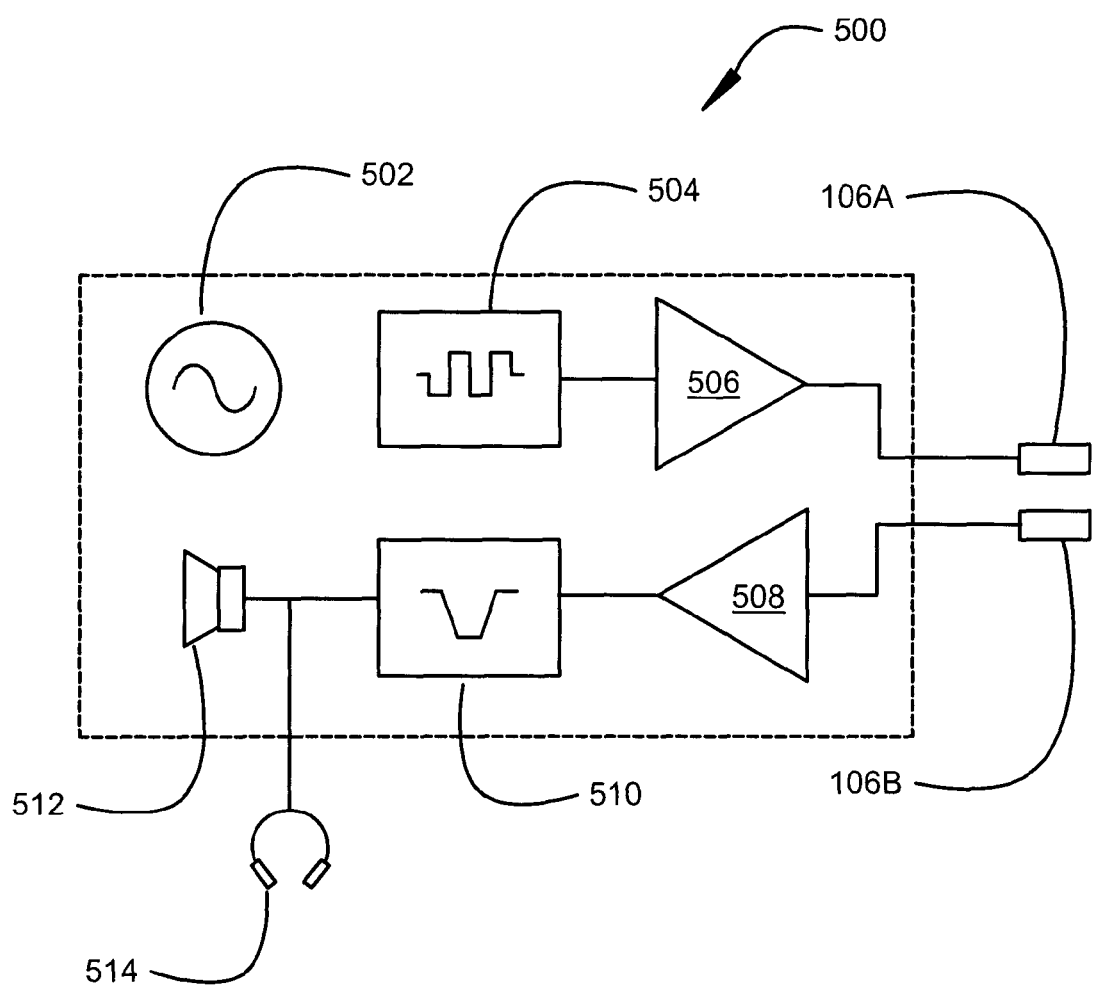
FIG. 5 is block diagram of a signal processing circuit according to embodiments of the present invention.

FIG. 5 shows a block diagram of catheter signal processing circuitry 500 that may be implemented according to various embodiments of the present invention. The circuitry 500 may be formed as a single functional unit, or may include physically and/or electrically separate functional units located on any part of the catheter 100 or connected apparatus. The circuitry 500 includes a power supply 502 that may include internal power sources (e.g., batteries) and/or power conditioning circuitry for external power.

A signal generator 504 may be used to generate various waveforms for use with the catheter sensing circuitry. The signal generator 504 may produce any manner of cyclic waveforms such as square, sinusoidal, and sawtooth waves. In addition, the signal generator 504 may provide random or pseudo-random waveforms such as white noise. The signal generator 504 may also provide user selectable frequency responses that can be applied to random or cyclic signal outputs.

The output of the signal generator 504 may be sent to an amplifier 506. The amplifier 506 provides an output power and impedance suitable for the transmitting transducer 106A. The amplifier 506 may include additional circuitry that provides filtering, equalization, selectable attenuation, and/or other signal conditioning features. The output of the amplifier 506 can be fed to the transmitting transducer 106A on the catheter 100.

The signal output from the transmitting transducer 106A is reflected off of anatomical features and detected at the receiving transducer 106B. The receiving transducer 106B may be coupled to an input amplifier 508 that is adapted for amplifying and conditioning signals from the receiving transducer 106B. The output of the amplifier 508 may be sent to a filter 510.

The filter 510 may provide any type of frequency or time based filtering to provide greater clarity of the reflected signal. For example, certain frequencies may be filtered out to remove extraneous noise, and other frequencies may be boosted to enhance reflected signal content of interest. The output of the filter 510 may be sent to any device used to interpret the signals. In this example, a speaker 512 and/or headphones 514 may be used to audibly detect changes in the reflected signals.

It will be appreciated that the catheter 100 may be arranged to operate in a passive detection mode, such that the signal generating elements of catheter 100 shown in FIG. 2 or the circuitry 500 shown in FIG. 5 are not required. It is appreciated that cardiac activity may produce a measurable energy parameter that varies as a function of the distance between a detection element of the catheter 100 and a destination vessel, particularly an opening to the destination vessel. For example, the catheter 100 may utilize components such as the receiving transducer 106B, input amplifier 508, filter 510, speaker 512, and headphones to effectively listen for acoustic signals generated by cardiac activity and, in particular, variations in such acoustic signals indicative of catheter tip movement towards or away from a destination vessel opening.

Referring again to FIG. 1, the arrangement of the catheter 100 for passive detection includes providing a transducer 106 at the distal end 104 of the flexible shaft 102. The transducer 106 may be configured to detect acoustic energy generated by cardiac activity. According to other embodiments, the transducer 106 may be configured to detect subsonic energy (e.g., <30 Hz), via an appropriate accelerometer, or blood temperature, via an appropriate temperature sensor.

The heart generates acoustic energy during contraction and relaxation processes, and this energy is transmitted through the blood vessels and fluids moved through the vessels. This energy is conducted along the vessels surrounding the heart and propagates, for example, towards an access vessel (e.g., coronary sinus 114) to a cardiac chamber, such as the right atrium 112. A discontinuity in the shape of the right atrium 112 relative to the ostium 124 of the coronary sinus 114 may cause heart sounds to be propagated to, and reflected in, the right atrium 112 in a manner similar to a speaker horn. As such, the magnitude of cardiac sounds in the right atrium 112 would change (e.g., increase) as the guiding catheter's transducer 106 advances toward the coronary sinus ostium 124.

In general, the fluid exiting the coronary sinus 114 into the right atrium 112 may have various energy parameters that may be detected by a passive detection configuration of the catheter 100. For example, the transducer 106 may include a temperature sensing transducer (e.g., thermocouple, thermister, fiber optic probe) that makes precise blood temperature measurements. In this example, deoxygenated blood flowing through the coronary sinus 114 is warmed after passing through the myocardial capillary bed. Therefore, this blood exits the coronary sinus 114 at a temperature higher than that of the relatively cooler blood flow coming from the lungs and present in the right atrium 112. Therefore, a catheter 100 having a distal temperature transducer 106 can be manipulated to follow the trail of warmer blood within the right atrium 112 in order to locate the coronary sinus 114.

The guiding catheter 100 may be used in any procedure that requires access through a convoluted pathway. Guiding catheters are commonly utilized in heart procedures because of the indirect access routes used. In one example, provided for purposes of illustration, a pacing lead is implanted into the coronary sinus of the heart. Still in reference to FIG. 1, the guiding catheter 100 is introduced through an incision 117 in the upper vasculature. The catheter shaft 102 can be introduced through this incision and into a guide vessel 116 of the vasculature. The distal end 104 of the catheter shaft 102 may enter into the right atrium 112 through the superior vena cava 118.

After the shaft's distal end 104 is located in the right atrium 112, the shaft 102 must be manipulated to place the distal end 104 in the coronary sinus 114. The opening (or ostium) of the coronary sinus 114 is located on a wall of the atrium 112 and typically involves considerable manipulation to place the catheter shaft 102 into the ostium. The shaft 102 may include a specially shaped distal end 104 designed for this task as well as a steering apparatus as previously described.

When attempting to locate the coronary sinus ostium, the physician may utilize the transducers 106 and proximal device 122 to assist in finding the vessel. The transmitting transducer(s) 106 send out an audio frequency signal and the receiving transducer(s) 106 detect echoes of those signals. The physician listens (or otherwise perceives) the reflected signals at the proximal device 108 to determine the location of anatomical features near to the distal tip 104. Depending on the types of audio signals used, the practitioner may listen for variations in magnitude (volume), harmonics, frequency response variations, phase variations or cancellations, additional noise, or any other detectable characteristics of the signal. The physician may also use a passive detection mode, where the transmitting transducer 106 is turned off for some period of time, or no transmitting transducer 106 is used at all. This use of passive detection may provide additional clues as to the location of the destination vessel, such as detecting sounds induced by flowing blood or structural changes or discontinuities in the heart. The passive detection mode may also be used with alternate transducers 106, such as a temperature sensing transducer.

The physician uses the signals detected from the transducers 106 to guide the flexible shaft 102 to its target location. In this example, the target location is the coronary sinus 114. Once the coronary sinus 114 has been located, the shaft 102 is advanced forward to access the coronary sinus 114 for purposes of the operation or therapy.

It will, of course, be understood that various modifications and additions can be made to the embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A catheter for locating a destination vessel of a heart, comprising:
   a flexible shaft having a proximal end and a distal end, the shaft being adapted for navigation to the heart;
   a transmitting transducer configured to emit an audio frequency signal;
   a receiving transducer configured to detect a first energy parameter associated with cardiac activity measurable at the distal end of the flexible shaft, the first energy parameter comprising a reflected signal from the audio frequency signal and varying as a function of a distance between the destination vessel and the distal end of the flexible shaft;
   a switch to selectively turn off the transmitting transducer while the receiving transducer is operating and to turn on the transmitting transducer while the receiving transducer is operating, wherein when the switch is turned on, the receiving transducer is configured to detect the first energy parameter and when the switch is turned off, the receiving transducer is further configured to detect a second energy parameter, the second energy parameter comprising an acoustic signal generated by cardiac activity; and
   a proximal device coupled to the receiving transducer, the proximal device arranged to produce a user perceivable representation of the first energy parameter, a variation of the first energy parameter indicating a relative proximity to the destination vessel to assist in navigating the distal end of the flexible shaft to the destination vessel.

2. The catheter of claim 1, further comprising an audio speaker coupled to the proximal device and configured to reproduce the acoustic signal.

3. The catheter of claim 1, wherein the receiving transducer comprises an audio transducer.

4. The catheter of claim 1, further comprising a steering mechanism, and wherein the distal end of the flexible shaft is deflectable by actuation of the steering mechanism at a proximal end of the catheter to steer the catheter in a desired direction.

5. The catheter of claim 1, further comprising a video display coupled to the proximal device and configured to provide a visual representation of the energy parameter.

6. A catheter for locating a destination vessel associated with one or more anatomical features of a heart, comprising:

a flexible shaft having a proximal end and a distal end, the shaft being adapted for navigation to the heart;
a sound transmitter configured to transmit an audio frequency signal from the distal end of the flexible shaft;
a switch to selectively turn on or off the sound transmitter;
a sound receiver configured to detect a reflected signal from the audio frequency signal and received at the distal end of the flexible shaft when the switch is turned on, the sound receiver also being configured to detect an acoustic signal generated by cardiac activity when the switch is turned off; and
a proximal device coupled to the sound receiver, the proximal device arranged to receive the reflected signal and produce a user perceivable representation of a variation in the reflected signal, the variation in the reflected signal indicating a presence of the anatomical features to assist in navigating the distal end of the flexible shaft to the destination vessel.

7. The catheter of claim 6, further comprising a steering mechanism, and wherein the distal end of the flexible shaft is deflectable by actuation of the steering mechanism at a proximal end of the catheter to steer the catheter in a desired direction.

8. The catheter of claim 7, wherein the steering mechanism comprises a steering tendon connected to an anchor member positioned at a distal portion of the catheter, the steering mechanism providing uni-directional steering of the catheter.

9. The catheter of claim 7, wherein the steering mechanism comprises at least two steering tendons connected to one or more anchor members positioned at a distal portion of the catheter, the steering mechanism providing bi-directional steering of the catheter.

10. The catheter of claim 6, further comprising an audio speaker coupled to the proximal device and configured to reproduce the reflected signal.

11. The catheter of claim 6, further comprising a video display coupled to the proximal device and configured to provide a visual representation of the reflected signal.

12. The catheter of claim 6, wherein the audio frequency signal comprises a cyclic signal.

13. The catheter of claim 6, wherein the audio frequency signal comprises a random signal.

14. A guiding catheter, comprising:
a flexible shaft having a proximal end and a distal end, the shaft being adapted for navigation to the heart;
sound transmission means for emitting an audio frequency signal from the distal end of the shaft;
a switch to selectively turn on or off the sound transmission means;
sound receiving means for detecting a reflected signal from the audio frequency signal at the distal end of the shaft when the switch is turned on, the sound receiving means being configured to also detect an acoustic signal generated by cardiac activity when the switch is turned off; and
processing means for receiving the reflected signal from the sound receiving means and presenting a user perceivable indication of a variation in the reflected signal, the variation in the reflected signal indicating the presence of an anatomical structure to assist in guiding the distal end of the flexible shaft.

15. The guiding catheter of claim 14, further comprising steering means for selectably deflecting the distal end of the flexible shaft to steer the catheter in a desired direction.

16. The guiding catheter of claim 14, further comprising audio playback means coupled to the catheter for audibly representing the reflected signal.

17. The guiding catheter of claim 14, further comprising display means coupled to the catheter for visually representing the reflected signal.

18. The guiding catheter of claim 14, wherein the audio frequency signal comprises a cyclic signal.

19. The guiding catheter of claim 14, wherein the audio frequency signal comprises a random signal.

20. A guiding catheter, comprising:
a flexible shaft having a proximal end and a distal end, the shaft being adapted for navigation to the heart;
a transmitting transducer configured to emit an audio frequency signal;
means for detecting a first energy parameter associated with cardiac activity measurable at the distal end of the flexible shaft, the first energy parameter comprising a reflected signal from the audio frequency signal and varying as a function of a distance between a destination vessel and the distal end of the flexible shaft, and further configured to detect a second energy parameter comprising an acoustic signal generated by cardiac activity when the transmitting transducer is off;
a switch to selectively turn on or off the transmitting transducer while the means for detecting the first energy parameter are operating, wherein when the transmitting transducer is turned on, the means for detecting is configured to detect the first energy parameter; and
means for presenting a user perceivable indication of a variation in the first energy parameter, the variation in the first energy parameter indicating a relative proximity to the destination vessel to assist in guiding the distal end of the flexible shaft.

21. The guiding catheter of claim 20, wherein the guiding catheter further comprises steering means for selectively deflecting the distal end of the flexible shaft to steer the catheter in a desired direction.

22. The guiding catheter of claim 20, wherein the detecting means comprises an audio signal detector, and the first energy parameter comprises a reflected signal from the audio frequency signal emitted by the transmitting transducer.

23. The guiding catheter of claim 20, further comprising a sleeve slidably coupled to the flexible shaft, the sleeve comprising the transmitting transducer.

24. The catheter of claim 1, further comprising a sleeve slidably coupled to the flexible shaft, the sleeve comprising the transmitting transducer.

25. The catheter of claim 6, further comprising a sleeve slidably coupled to the flexible shaft, the sleeve comprising the sound transmitter.

26. The catheter of claim 14, further comprising a sleeve slidably coupled to the flexible shaft, the sleeve comprising the sound transmission means.

27. The catheter of claim 1, wherein the distal end of the flexible shaft is shaped for placement in a coronary sinus ostium of the heart.

28. The catheter of claim 6, wherein the distal end of the flexible shaft is shaped for placement in a coronary sinus ostium of the heart.

29. The catheter of claim 14, wherein the distal end of the flexible shaft is shaped for placement in a coronary sinus ostium of the heart.

30. The catheter of claim 20, wherein the distal end of the flexible shaft is shaped for placement in a coronary sinus ostium of the heart.

* * * * *